US006238361B1

(12) United States Patent
Poirier

(10) Patent No.: US 6,238,361 B1
(45) Date of Patent: May 29, 2001

(54) TRACTION AND ABDUCTION APPARATUS FOR TREATING THE LEGG-CALVES PERTHES DISEASE

(76) Inventor: François Poirier, 210, rue St-Francois Ste-Pie-de-Bagot Québec (CA), J0H 1W0

(*) Notice: Subject to any disclaimer, the term of this patent is extended or adjusted under 35 U.S.C. 154(b) by 0 days.

(21) Appl. No.: 09/379,374

(22) Filed: Aug. 23, 1999

(51) Int. Cl.[7] .......... A61F 5/00
(52) U.S. Cl. .......... 602/33; 606/241
(58) Field of Search .......... 602/23–25, 28–29, 602/37–36, 39; 128/882; 606/237, 240, 241, 244; 5/621, 624, 648–651; 482/907

(56) References Cited

U.S. PATENT DOCUMENTS 1,456,030 * 5/1923 Molby .......... 128/870
1,456,031 * 5/1923 Molby .......... 128/870 X
2,588,411 * 3/1952 Robinson .......... 602/24
2,798,481 * 7/1957 Matthews .......... 606/241
2,821,976 * 2/1958 Lindstrom .......... 602/33
3,728,999 * 4/1973 Thompson .......... 602/36
5,148,800 * 9/1992 Pecheux .......... 601/29
5,387,186 * 2/1995 Edland .......... 602/36
5,681,272 * 10/1997 Lee .......... 602/32

FOREIGN PATENT DOCUMENTS

2355848 * 5/1974 (DE) .......... 602/33
1189417 * 4/1970 (GB) .......... 602/32
738615 * 6/1980 (SU) .......... 602/32

OTHER PUBLICATIONS

Roy, Dennis, "Current Concepts in Legg–Calve–Perthes Disease," Pediatric Annals (28:12/Dec. 1999), p. 748–752.*
Chick–Leinbach crib fracture set, The Journal of Bone and Joint Surgery, Jun. 1955, p. 44.*

* cited by examiner

*Primary Examiner*—Mickey Yu
*Assistant Examiner*—Denise Pothier
(74) *Attorney, Agent, or Firm*—Francis Martineau

(57) ABSTRACT

An orthopedic apparatus for treating a child afflicted with the Legg Calves Perthes disease. The apparatus includes a telescopic cross-bar adapted to be attached at each ends to the feet of a patient's resting on a bed, to keep his legs spread apart. A post upstands from the foot of the bed and carries pulleys; a rope is trained on the pulleys and is connected at one end to the center of the cross-bar while a weight is attached to the other end of the rope. A constant pull is exerted on the patient's legs while the legs are kept spread apart. The amounts of pull and of leg spread are both adjustable. The present apparatus is destined to be used mainly at the child's home, but only shortly at the hospital, under the supervision of the parents. This apparatus is foldable and is easily carriable in a relatively small case.

7 Claims, 2 Drawing Sheets

50
46
22
20
54
16
56
14
48
18
58
26
82
40
6
52
26
28
8
30
8
39
44
10
43
42
6
82
4
38
36
2
60

46
50
22
20
20
24
18

14
12
26
M
28
30
8
32
6
10

TRACTION AND ABDUCTION APPARATUS FOR TREATING THE LEGG-CALVES PERTHES DISEASE

FIELD OF THE INVENTION

The present invention relates to an orthopedic apparatus for treating children suffering from the Legg Calves Perthes disease. This disease affects the hips of children and more particularly the joint between the hip bone and the thigh bone. The head of the thigh bone and the cartilage between this head and the acetabulum disintegrates. The acetabulum is the cavity in the hip bone in which the head of the thigh bone fits.

BACKGROUND OF THE INVENTION

Previous treatment for the Legg Calves Perthes disease usually consists of placing each leg of the patient in a cast, both legs held in abduction and internal rotation by a cross-bar extending between the two casts. This system immobilises the patient in a particular position for a long time. Due to the young age of the patients asnd the restlessness thereof associated with young age and the uncomfortable prospect of remaining several weeks in bed doing nothing, the treatment is often only partly applied and thus not fully successful. The reason for this unsuccessful treatment with conventional apparatuses is that the young patient will tend to voluntarily release relatively frequently the cross-bar from themselves, since it is physically possible for them to reach out to this cross-bar from their bed-laying condition. Indeed, the young patient, not being fully conscious at that age (usually around 10 years old) that for the treatment to be successful, constancy in the leg pulling action thereof during the several weeks long treatment period is a prerequisite.

Leg pulling apparatus are known such as the one described in U.S. Pat. No. 1,021,688 issued Mar. 26, 1912 entitled "LEG PULLING APPARATUS" by the inventor L. J. Le Jeune. This apparatus exerts an adjustable traction on the patient's legs but does not provide any abduction, namely drawing away from the median line of a bone or muscle from an adjacent part or limb.

OBJECTS OF THE INVENTION

It is therefore the main object of the present invention to provide an improved orthopedic device for treating the Legg Calve Perthes disease, in which the patient's legs are both pulled and spread apart from one another.

Another object of the present invention is to provide an apparatus of the character described in which the legs can be progressively spread apart from one another during the treatment and the pulling force gradually increased.

Another object of the present invention is to provide an apparatus of the character described which is foldable and is of light construction so as to be easily be carried from one place to another.

Another object of the present invention is to provide an apparatus of the character described which can be quickly and easily set up at the foot of a patient's bed.

SUMMARY OF THE INVENTION

This invention is directed to an orthopedic apparatus for treating the Legg Calves Perthes disease, which comprises a patient's leg spreading bar, attachment devices carried by the ends of said bar for attaching said bar to patient's legs and keeping them spread apart and a leg pulling system, to exert constant pull on the center of said bar in a direction away from said patient, and preferably generally within the sagital plane thereof.

Preferably, the bar is formed of telescopic sections and includes a tightener to releasably lock said sections in telescopically adjusted position.

Preferably, the system includes a collar slidably surrounding said bar and a collar tightener to tighten said collar in longitudinally adjusted position on said bar.

Preferably, the attachment devices include plates sized to be applied flat against the soles of the patient's feet, a universal pivot releasably connecting said plates to said ends of said bars and locking devices releasably locking said plates in adjusted inclined position relative to said bar.

Preferably, each of said attachment devices includes a U-shape traction plate forming two spaced apart plate sections to receive a bandage attached to a patient's leg, one of said plate sections having an inturned lip to retain said bandage between said plate sections.

Preferably, the leg pulling system comprises a post, vertically spaced upper and lower idle pulleys carried by said post, a rope passing over said pulleys having a first and a second rope end portion, said first rope end portion hanging from said upper pulley, a weight attached to said first rope end portion, said second rope end portion connected to said patient's leg spreading bar at the center thereof.

Preferably, said leg pulling system further includes a flat base frame adapted to be inserted under the mattress of a bed with said post upstanding therefrom at the foot of said mattress.

Preferably, said post is pivotally connected to said base frame and a locking device locks said post at an adjusted angle relative to said base frame.

Preferably, said base frame has a U-shape defining a bight and two spaced apart legs, said post formed of two spaced parallel members and cross bars rigidly interconnecting said spaced parallel members, said pulleys being rotatably carried by said spaced parallel members and located between the same.

Preferably, said post has an upright lower portion and an upper cantilever portion making a general right angle with said lower portion, said upper pulley carried by said cantilever portion, said lower pulley carried by said lower portion.

Preferably, said weight includes a flexible waterproof bag to hold water.

Preferably, said lower portion and said cantilever portion are detachable from each other.

The invention also relates to a method of use of an orthopedic apparatus for treating the Legg-Calves Perthes disease, the apparatus of the type comprising a patient's leg spreading telescopic bar, leg attachment devices carried by each end of said bar for attaching said bar to the patient's legs and keeping them spread apart and a leg pulling system including a support post to exert a constant pull on the center of said bar in a direction away from said patient, the method comprising the following steps:

inserting said base frame at the foot of a bed under the bed mattress, with the post upstanding from the foot end of the bed at an adjusted inclined position;

attaching each leg attachment device to a respective patient's leg under the foot, adjusting the overall length of the legs spreading bar to the patient's size; and progressively increasing the overall length of the legs spreading bar during the duration of treatment, while concurrently recentering the telescopic bar so that the pulling force remain generally within the patient's sagital plane, each time the overall length of the telescopic bar is changed.

BRIEF DESCRIPTION OF THE DRAWINGS

In the annexed drawings, wherein like reference characters indicated.

DETAILED DESCRIPTION OF THE PREFERRED EMBODIMENT

Figure 1:
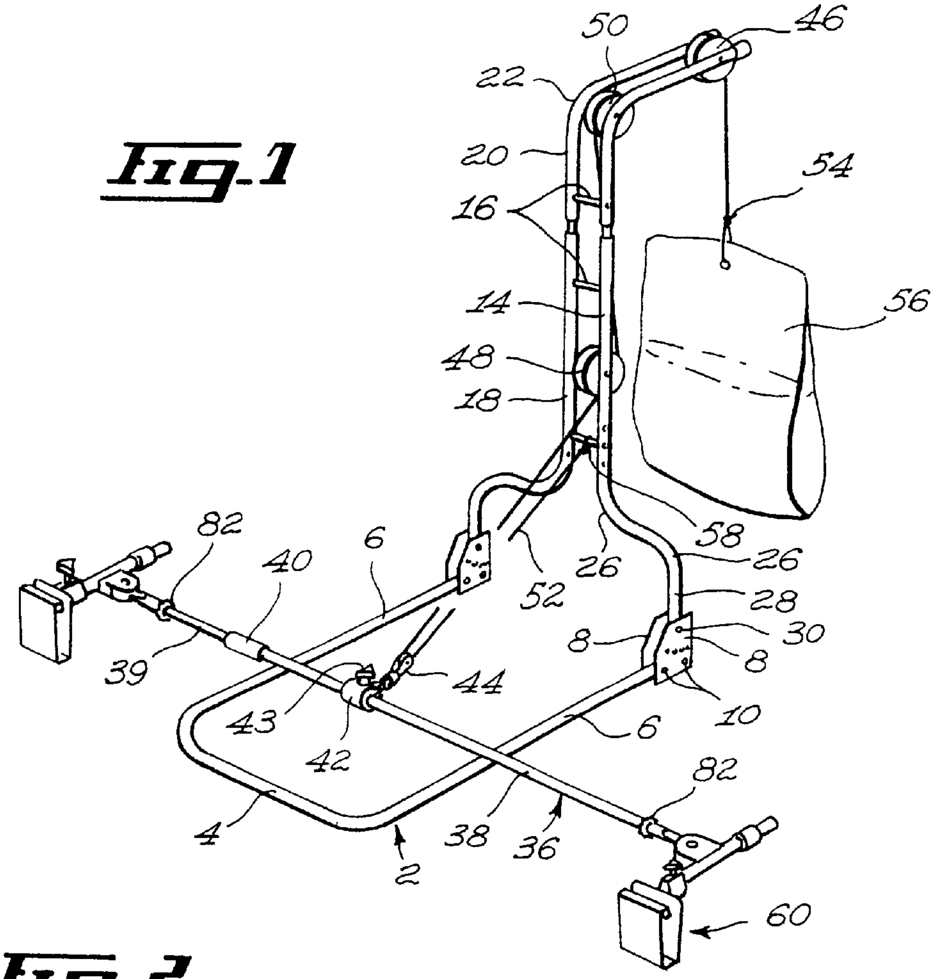
FIG. 1 is a perspective view of the apparatus in accordance with the invention, with the weight consisting of a flexible pouch filled with water.

The apparatus of the invention comprises a base frame 2 formed of a tubular member having a U-shape defining a bight 4 and two parallel, spaced legs 6 fitted at each free end with a pair of upright plates 8, 8, secured thereto by rivets 10.

Figure 2:
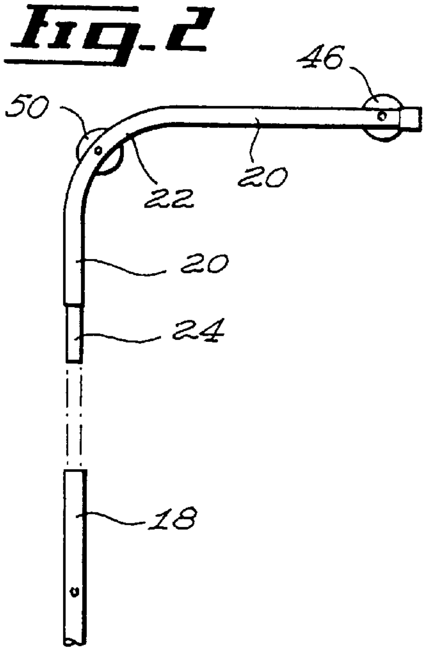
FIG. 2 is a partial side elevation of the post made of a lower upright portion and an upper cantilever portion.
Figure 3:
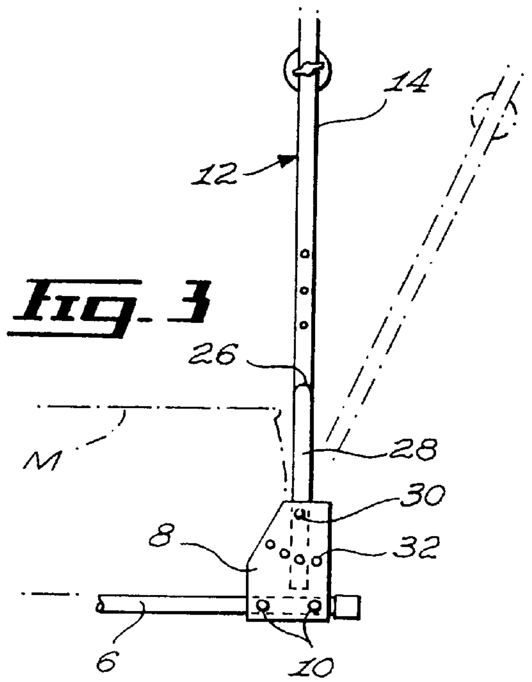
FIG. 3 shows in full line a partial side elevation of post and base frame inserted under a bed mattress and suggesting in phantom lines how the post can be adjustably inclined.

The apparatus further includes a post 12 formed of two spaced, parallel, tubular members 14 interconnected by cross-bars 16. The post define a lower upright portion 18 and a separate upper cantilever portion 20. Cantilever portion 20 has an intermediate rectangular bend 22. Portions 18 and 20 are releasably joined together by a a reduced diameter joining end portion 24 as shown in FIG. 2. The lower portion 18 forms for each member 14 a double bend 26 ended by a free end portion 28 which is pivoted at 30 between the two plates 8. These plates have a series of holes 32 concentric with the pivot 30 as shown in FIG. 3 for receiving a locking pin to adjustably lock the post 12 in a desired inclination as shown in FIG. 3.

A leg spreading bar 36 is provided in accordance with the present invention. This bar 36 is composed of two telescopic sections 38, 39 adjustably fitted one into the other and tightened in adjusted position by a tightener 40 of conventional construction.

Figure 6:
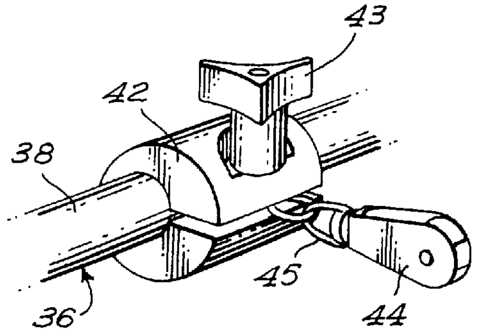
FIG. 6 is a partial perspective view of the central collar on the cross-bar, at an enlarged scale.
Figure 7:
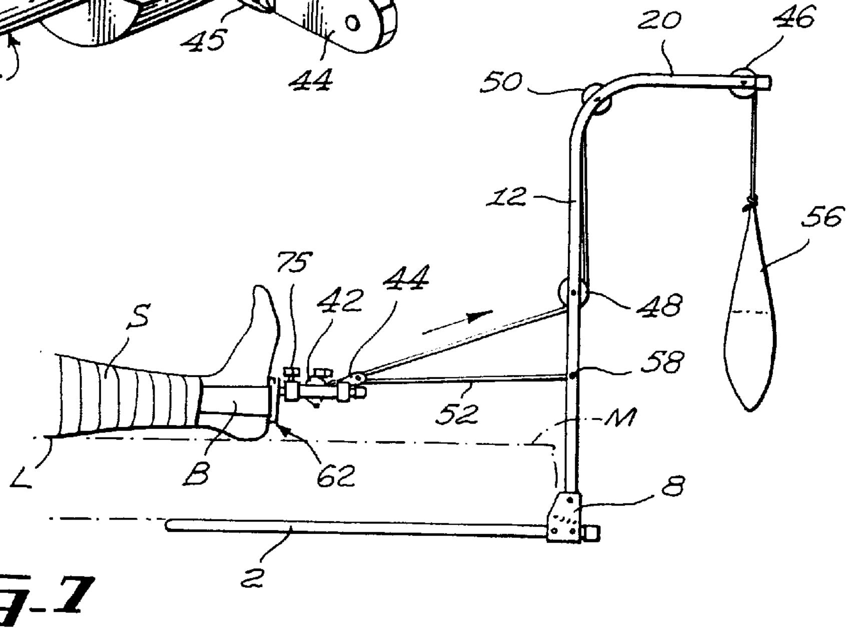
FIG. 7 is a side elevation of the apparatus in operative position, showing a patent leg pulled horizontally by the present apparatus.

A split collar 42, provided with a collar tightener 43 as shown in FIG. 6, is slidably fitted on one of the telescopic section 38 adjusted and secured centrally of the bar 36 by means of a collar tightener 43. A return pulley 44 is attached to collar 42 by means of chain link 45 attached to the bolt of the tightener 43. An upper pulley 46, a lower pulley 48 and an intermediate pulley 50 are mounted on post 12, being freely rotatable on cross-pins at the outer end of the cantilever portion 20, on the lower portion 18 and at the bend 22 of the cantilever portion 20 respectively.

A flexible rope 52 is trained on the pulleys 44, 46, 48 and 50. The rope 52 has a first end 54 depending from pulley 46 and attached to a flexible waterproof bag 56 designed to hold an adjusted quantity of water. The bag can be emptied after each treatment, if so desired, for measured water volume refill. The second end 58 of the rope 52 is attached to the lowermost cross-bar 16 after have been trained on the return pulley 44.

Figure 4:
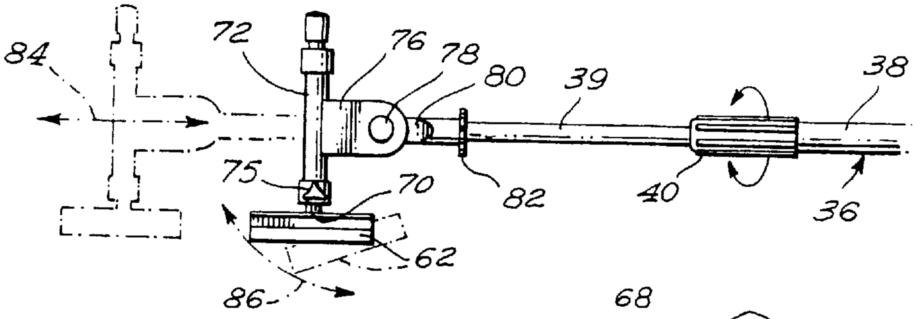
FIG. 4 is a top plan view of one end portion of the telescopic, leg spreading cross-bar, suggesting in phantom lines the telescopic extension capability thereof.
Figure 5:
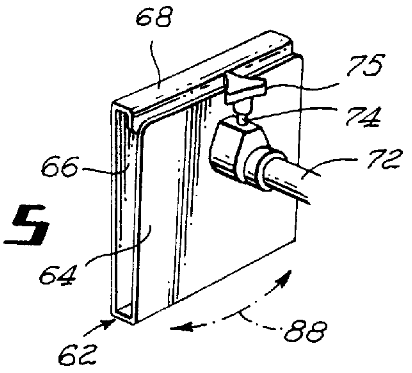
FIG. 5 is an enlarged partial perspective view of one of the leg attachment device at each end of the cross-bar.

Leg spreading cross-bar 36 carries at each end, a patient's leg attachment device 60. Each device comprises a U-shape plate 62 sized to be applied flat against the sole of the patient's foot L and including an inner plate section 64 and an outer plate section 66, the latter being fitted with an inturned lip 68 at its outer edge as shown in FIGS. 4 and 5. The inner plate section 64 is fixed to a center rod 70 fitted within a sleeve 72 so that U-shape plate 62 can be rotated with respect to sleeve 72 and locked in adjusted position by means of a bolt 74 having a knob 75.

Sleeve 72 has a side leg 76 which is pivoted at 78 to outer end 80 of bar 36. A knurled collar 82 surrounds and is fixed to outer end 80.

It follows that the two U-shape plates 62 can be spread apart more or less from each other in accordance with double arrow 84 of FIG. 4, and pivoted about pivots 78 so as to be in diverging or converging condition with respect to each other in accordance with double arrow 86 in FIG. 4.

Finally, the rotational position of each U-plate 62 can be changed in sleeve 72 and set by bolt 74 in accordance with double arrow 88 shown in FIG. 5.

The apparatus of the invention is used as follows:

The base frame 2 is first inserted at the foot of the bed under the mattress M with the post 12 upstanding from the foot end of the bed at an adjusted inclined position as shown in FIG. 3.

Then, each U-shape plate 62 is attached to the respective patient's leg L under the foot, by means of a bandage B and a strapping S in usual manner, with the bandage prevented from accidental removal from its intended place between the two plates sections 64 and 66 due to the presence of the lip 68. Moreover, since lip 68 is located against the underface sole of the child's foot, i.e. away from the hands of the young bed-laying patient, the latter will not be able by himself/herself to reach out and voluntarily release the present apparatus from his/her bed laying position. Only a medical staff personnel or other supervisory parental authority will be able to reach out to the patient's foot sole from ahead of the bed mattress—a much improved guarantee of thorough leg pulling treatment.

The overall length of the legs spreading bar 36 is thereafter adjusted to the patient's size and also progressively increased during the treatment, which can last several months. Each time the overall length of the telescopic bar 36 is changed, the collar 42 is repositioned to be at the center of the bar 36, that is mid-way between the two U-shaped plates 62. The angular position of these plates 62 in all direction can be adjusted so as to impart suitable rotation of the patient's legs L with respect to one other. While the legs are kept spread apart, a gentle pull is exerted on the cross-bar 36 by means of the pulling device including the rope 52 and water filled bag 56. The amount of water in bag 56 can be progressively increased or decreased in accordance with the protocol of the treatment.

Since the apparatus of the invention is designed to be used at home, under the supervision of the treated child's parents or of visiting medical personnel, the apparatus is foldable and can be carried in a relatively small case. It is also light weight and the water bag can be emptied of water after each treatment.

I claim:

1. An orthopedic apparatus for treating the Legg-Calves Perthes disease comprising:

A patient's leg spreading bar, leg attachment devices carried by each end of said bar for attaching said bar to the patient's legs and keeping them spread apart, a leg pulling system mounted on the center of said leg spreading bar to exert a constant pull on the center of said bar in a direction away from the patient; said leg pulling system comprising a post, vertically paced, upper and lower idle pulleys carried by said post, a rope passing over said pulleys and having a first and a second rope end portion, said first rope end portion hanging from said upper pulley, a weight attached to said first rope end portion, said second rope end portion connected to said patient's leg spreading bar at the center thereof, wherein said constant pull on the center of the bar is in a direction generally within the patient's sagital plane;

a flat base frame, said post secured to and upstanding from said base frame, said base frame adapted to be inserted under the mattress of a bed with said post upstanding therefrom at the foot of the mattress; said post being pivotally connected to said base frame;

and a locking device to lock said post at an adjusted angle relative to said base frame;

wherein said base frame has a U-shape defining a bight and two spaced apart legs, said post formed of two spaced parallel members and cross bars interconnecting, said spaced parallel members, said pulleys being rotatably carried by said spaced parallel members and located between the same.

2. An orthopedic apparatus as defined in claim 1, wherein said post has an upright lower portion and an upper cantilever portion making a general right angle with said lower portion, said upper pulley carried by said cantilever portion, said lower pulley carried by said lower portion.

3. An orthopedic apparatus as defined in claim 1, wherein said weight includes a flexible waterproof bag to hold water.

4. An orthopedic apparatus as defined in claim 3, wherein said leg spreading bar is formed of telescopic sections and further including a tightener to releasably lock said telescopic sections in telescopically adjusted position, a collar slidably surrounding said telescopic bar, a collar tightener to tighten said collar in adjusted position centrally of said leg spreading bar and a return pulley carried by said collar on which said second rope end portion is trained and secured to one of said cross bars.

5. An orthopedic apparatus as defined in claim 4, wherein said lower portion and said cantilever portion are detachable from each other.

6. An orthopedic apparatus as defined in claim 5, wherein each of said attachment devices includes a U-shaped traction plate defining two spaced plates sections to receive a bandage attached to a patient's leg, one of said plate sections having an inturned lip to retain said bandage between said plate sections.

7. A method of use of an orthopedic apparatus for treating the Legg-Calves Perthes disease, the apparatus of the type comprising:

a base frame, a patient's leg spreading telescopic bar;

leg attachment devices carried by each end of said bar for attaching said bar to the patient's leg and keeping them spread apart; and a leg pulling system including a support post adjustably pivoted to said base frame to exert a constant pull on the center of said bar in a direction away from said patient, the method comprising the following steps:

inserting said base frame at the foot of a bed under the bed mattress, with the post upstanding from the foot end of the bed at an adjusted inclined position;

attaching each leg attachment device to a respective patient's leg under the foot;

the adjusting the overall length of the legs spreading bar to the patient's size; and progressively increasing the overall length of the legs spreading bar during the duration of treatment, while concurrently recentering said leg spreading telescopic bar so that the pulling force remain generally within the patient's sagital plane, each time the overall length of the telescopic bar is changed.

* * * * *